United States Patent
Fujishiro et al.

Patent Number: 6,153,399
Date of Patent: *Nov. 28, 2000

[54] DETERMINING ASCORBIC ACID USING ASOD AND LEUCO CHROMOGEN

[75] Inventors: Kinya Fujishiro; Katsuyuki Taga, both of Sunto-gun; Norihito Aoyama, Gotemba; Akira Miike, Sunto-gun, all of Japan

[73] Assignee: Kyowa Medex Co., Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/142,916
[22] PCT Filed: Jan. 20, 1998
[86] PCT No.: PCT/JP98/00196
  § 371 Date: Sep. 18, 1998
  § 102(e) Date: Sep. 18, 1998
[87] PCT Pub. No.: WO98/31829
  PCT Pub. Date: Jul. 23, 1998

[30] Foreign Application Priority Data

Jan. 20, 1997 [JP] Japan .................. 9-007305

[51] Int. Cl.[7] .............. C12Q 1/28; C12Q 1/26; C07D 279/28
[52] U.S. Cl. .............. 435/28; 435/25; 436/93; 544/35; 544/37; 544/38
[58] Field of Search .............. 435/28, 25, 190, 435/962, 975; 436/93, 825; 544/35, 37, 38

[56] References Cited

U.S. PATENT DOCUMENTS

| | | | |
|---|---|---|---|
| 4,879,383 | 11/1989 | Sakata et al. | 544/37 |
| 5,441,872 | 8/1995 | Tulley | 435/25 |
| 5,612,208 | 3/1997 | Nakanishi et al. | 435/189 |
| 5,783,382 | 7/1998 | Aoyama et al. | 435/4 |

FOREIGN PATENT DOCUMENTS 06169796  6/1994  Japan .................. C12Q 1/26

OTHER PUBLICATIONS

Uchiyama et al. Selective Biocoulometry of Vitamin C Using Dithiothreitol, N–Ethylmaleimide, and Ascorbate Oxidase. Anal. Chem. 63 (20), pp. 2259–2262. (Oct. 1991).

Casella et al. Rapid Enzymatic Method for Vitamin C Assay in Fruits and Vegetables Using Peroxidase. J. Food Science. 54 (2), pp. 374–375, 378. (1989). No month given.

*Primary Examiner*—Michael P. Woodward
*Assistant Examiner*—Marjorie A. Moran
*Attorney, Agent, or Firm*—Fitzpatrick, Cella, Harper & Scinto

[57] ABSTRACT

A reagent, kit and method for the quantative determination of ascorbic acid in a sample uses ascorbate oxidase which catalyzes the reaction of reduced ascorbic acid to oxidized ascorbic acid and hydrogen peroxide. Ascorbic acid in the sample is reacted with oxygen in the presence of the ascorbate oxidase, chromogen and peroxidase. Absorbance is determined and compared with a known calibration curve. The chromogen is preferably a compound of the formula (I) or (II)

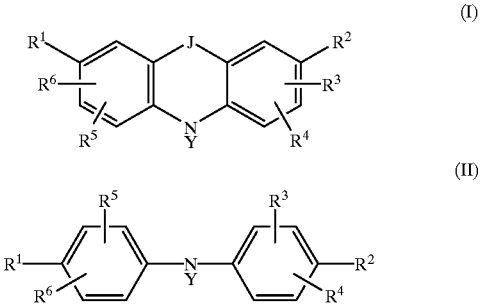

21 Claims, 2 Drawing Sheets

DETERMINING ASCORBIC ACID USING ASOD AND LEUCO CHROMOGEN

TECHNICAL FIELD

The present invention relates to a method, a reagent and a kit for the quantitative determination of ascorbic acid.

BACKGROUND ART

Ascorbic acid, which is also called vitamin C, is an important vitamin for its shortage in vivo causes scorbutus, etc., and the relation between ascorbic acid and senility has been noted in recent years. Therefore, the determination of ascorbic acid is recognized as important.

Previous methods for the quantitative determination of ascorbic acid include chemical methods such as the hydrazine method and instrumental methods such as high performance liquid chromatography. However, these known methods have the disadvantages of involving complicated procedures and requiring many hours for the determination.

Recently, ascorbate oxidase (hereinafter referred to as ASOD) was discovered which catalyzes oxidation reaction of reduced ascorbic acid in the presence of oxygen to form oxidized ascorbic acid and hydrogen peroxide. Ascorbic acid in a sample is determined by measuring the amount of oxygen consumed or the amount of hydrogen peroxide formed by this enzyme reaction [JP-A-209770/94, JP-A-23971/96 (EP-A-682116)].

JP-A-209770/94 discloses a chemical method as the specific method for the determination of hydrogen peroxide, but does not disclose a method using peroxidase. JP-A-23971/96 (EP-A-682116) discloses a method for the determination of hydrogen peroxide which comprises reacting hydrogen peroxide, in the presence of peroxidase, with a chromogen comprising a hydrogen donor such as phenol or a Trinder's reagent and a coupler such as 4-aminoantipyrine to form a pigment, and then measuring the absorbance of the reaction solution colored by the formed pigment. This is a method for the determination of hydrogen peroxide formed which is carried out after the reaction for forming hydrogen peroxide is completed and reduced ascorbic acid is completely converted into oxidized ascorbic acid.

Generally, it is known that the presence of reducing substances such as ascorbic acid and dithiothreitol disturbs a reaction for forming a pigment by the use of peroxidase. Therefore, it is necessary to carry out the reaction for forming a pigment only after reduced ascorbic acid in a sample is completely oxidized by the action of ASOD and the formation of hydrogen peroxide is completed. In this method, despite of the utilization of an enzyme reaction, chemically unstable hydrogen peroxide must be accumulated once in the reaction solution.

Biological samples contain reducing substances such as uric acid, catalase, bilirubin and hemoglobin which consume the formed hydrogen peroxide. Therefore, the above method in which hydrogen peroxide is accumulated can not give accurate data having reproducibility. Further, the method involves complicated procedures and requires many hours for the determination.

In a living organism, oxidized ascorbic acid exists along with reduced ascorbic acid, and the determination of total ascorbic acid composed of reduced ascorbic acid and oxidized ascorbic acid is also clinically important.

Total ascorbic acid can be determined by converting oxidized ascorbic acid into reduced ascorbic acid with a reducing agent such as dithiothreitol and measuring reduced ascorbic acid using ASOD. However, the method in which hydrogen peroxide formed is reacted with a chromogen in the presence of peroxidase and the formed pigment is determined has the disadvantage that the formation of the pigment is disturbed because the chromogen is influenced by a coexisting reducing agent. To solve this problem, elimination of the remaining reducing agent from the reaction solution prior to the determination of hydrogen peroxide becomes necessary, which makes the procedures complicated.

JP-A-29297/82 (U.S. Pat. No. 4,384,042) and JP-A-218069/85 disclose methods for the determination of an analyte in a sample wherein the reaction of the sample with oxidase acting on the analyte as the substrate to form hydrogen peroxide (hereinafter referred to as the hydrogen peroxide-forming reaction) and the reaction of the hydrogen peroxide with a chromogen to form a pigment (hereinafter referred to as the pigment-forming reaction) are carried out in the same reaction system. However, in these publications, there is no disclosure of a method wherein the oxidation of reduced ascorbic acid with ASOD and the reaction of the formed hydrogen peroxide with a chromogen to form a pigment are carried out in the same reaction system.

As previously described, the formation of a pigment is inhibited in the presence of a reducing substance such as ascorbic acid, and thus it was considered impossible to carry out the hydrogen peroxide-forming reaction and the pigment-forming reaction in the same reaction system. However, it has been found that there exist chromogens which are not affected by a reducing substance under specific conditions in the determination process, and the present invention has been completed based on this finding.

DISCLOSURE OF THE INVENTION

An object of the present invention is to provide a simpler method for the determination of ascorbic acid which is applicable to screening in clinical assays and which is capable of analyzing a large number of samples at the same time, and also provide a reagent and a kit for the determination of ascorbic acid suitable for use in such a method.

According to the present invention, ascorbic acid can be determined by a method for the determination of ascorbic acid in a sample using ascorbate oxidase which catalyzes the reaction of reduced ascorbic acid with oxygen to form oxidized ascorbic acid and hydrogen peroxide (hereinafter the enzyme is referred to as ASOD), wherein the reaction of reduced ascorbic acid with oxygen in the presence of ASOD to form oxidized ascorbic acid and hydrogen peroxide and the reaction of the formed hydrogen peroxide with a chromogen in the presence of peroxidase to form a pigment are carried out in an aqueous medium in the same reaction system and then the formed pigment is determined (this method is hereinafter referred to as Method A).

Total ascorbic acid in a sample can be determined by carrying out the above Method A in the presence of a reducing agent which can convert oxidized ascorbic acid into reduced ascorbic acid. In this method, oxidation and reduction are repeated because oxidized ascorbic acid formed by the enzyme reaction is converted again into reduced ascorbic acid with the reducing agent. Therefore, total ascorbic acid at a relatively low concentration can be easily determined by this method (the method is hereinafter referred to as Method B).

Total ascorbic acid in a sample can also be determined by the above Method A which further comprises the step of reducing oxidized ascorbic acid in the sample with a reducing agent and the step of deactivating the remaining reducing agent (this method is hereinafter referred to as Method C).

The present invention provides a reagent for the determination of ascorbic acid comprising ASOD, a chromogen and peroxidase (hereinafter referred to as Reagent A).

The present invention also provides a reagent for the determination of ascorbic acid comprising the components of Reagent A and a reducing agent which is capable of converting oxidized ascorbic acid into reduced ascorbic acid (hereinafter referred to as Reagent B).

Furthermore, the present invention provides a reagent for the determination of ascorbic acid comprising the components of Reagent B and a compound which is capable of deactivating the reducing agent (hereinafter referred to as Reagent C).

In the above Reagents A, B and C, any two or more of the components may be contained in the form of a composition.

The present invention also provides a kit which is convenient for the determination of ascorbic acid.

The reagent for the determination of the present invention can be used not only in the form of a single reagent but also in the form of a kit consisting of plural reagents according to the storage stability, operability and supply form of reagents. The kit can be prepared by selecting the necessary components from the above components and the compositions comprising any two or more of the components. A combination which is not suitable as a composition such as a combination of a reducing agent and a compound which deactivates the reducing agent should be avoided. Examples of the kits are shown below.

A kit for Reagent A consists of a reagent comprising ASOD and peroxidase and a reagent comprising a chromogen (hereinafter referred to as Kit A).

A kit for Reagent B consists of a reagent comprising a chromogen and a reducing agent and a reagent comprising ASOD and peroxidase (hereinafter referred to as Kit B).

A kit for Reagent C consists of a reagent comprising a chromogen and a reducing agent and a reagent comprising ASOD, peroxidase and a compound capable of deactivating the reducing agent (hereinafter referred to as Kit C).

The reagent for the determination and the reagents which constitute the kit for the determination may be in the form of a dry product, but they may be prepared in the form of a liquid reagent by adding an aqueous medium to omit the preparation process of the reagents before each use.

Any of the above reagents for the determination and the reagents in the kit may further comprise a buffer agent, an enzyme-activating agent, a preservative, a stabilizer, a surfactant, etc., if necessary. These components can be added to a reaction solution in the determination process.

The methods for the determination of reduced ascorbic acid of the present invention are described in detail below.

In Method A, a sample containing reduced ascorbic acid, ASOD, a chromogen and peroxidase is added to an aqueous medium such as a buffer solution, and the mixture is subjected to reaction at 20–50° C. for 1–15 minutes. The change in absorbance of the reaction solution colored by the formed pigment is measured to determine the amount of ascorbic acid from the calibration curve previously made using solutions containing reduced ascorbic acid at known concentrations.

ASOD requires oxygen as a substrate, but oxygen supply is not necessary because oxygen usually exists in the aqueous medium. However, it is desirable to shake or stir the reaction solution containing reduced ascorbic acid, a chromogen, ASOD and peroxidase prior to the reaction.

In Method B, a reducing agent capable of converting oxidized ascorbic acid into reduced ascorbic acid is added to a sample containing ascorbic acid, and then the resulting reaction mixture is subjected to the steps of Method A to determine the total amount of reduced ascorbic acid and oxidized ascorbic acid in the sample.

The determination according to Method B can be carried out more simply by adding Reagent B or Kit B to a sample containing ascorbic acid, subjecting the resulting mixture to reaction in an aqueous medium at 20–50° C. for 3–30 minutes, and measuring the change in absorbance of the reaction solution colored by the formed pigment to determine the amount of ascorbic acid from the previously-made calibration curve.

In Method B, oxidized ascorbic acid is converted into reduced ascorbic acid with the reducing agent in the course of reaction, which is then converted into oxidized ascorbic acid by the enzyme reaction. Therefore, the determination of ascorbic acid can be carried out with improved sensitivity through repeated oxidations and reductions. By the use of this method, total ascorbic acid contained in a sample at a low concentration can be determined.

In Method C, a reducing agent capable of converting oxidized ascorbic acid into reduced ascorbic acid is added to a sample containing ascorbic acid, and the mixture is subjected to reaction at 20–50° C. for 1–15 minutes to convert oxidized ascorbic acid into reduced ascorbic acid. Then, a compound capable of deactivating the reducing agent is added and the mixture is subjected to reaction at 20–50° C. for 1–15 minutes to deactivate the remaining reducing agent. The resulting reaction mixture is subjected to the steps of Method A to determine the total amount of reduced ascorbic acid and oxidized ascorbic acid in the sample.

In carrying out the determination according to this method, the reaction to deactivate the reducing agent and the reaction for the determination of reduced ascorbic acid by Method A can be carried out in the same reaction system. That is, total ascorbic acid can be determined by adding the reagent comprising a chromogen and a reducing agent of Kit C to a sample containing ascorbic acid to convert oxidized ascorbic acid into reduced ascorbic acid, adding the other reagent of Kit C to carry out the enzyme reaction, and then measuring the change in absorbance of the reaction solution.

The determination of the pigment formed by the coloration reaction is carried out by measuring the change in absorbance, usually the increase in absorbance, by the use of, for example, a commercially available spectrophotometer at a wavelength of 400–750 nm, preferably at the maximum absorption wavelength of the chromogen with a reagent blank as a control. A solution containing reduced ascorbic acid at a known concentration is subjected to the same reaction as described above and the change in absorbance is measured to prepare a calibration curve. An unknown amount of reduced ascorbic acid and an unknown total amount of reduced ascorbic acid and oxidized ascorbic acid can be determined using this calibration curve.

The components of a reaction solution are used at the concentrations shown below.

The chromogen is used in an equimolar amount with reduced ascorbic acid in the reaction solution or more, preferably 1–10000 molar equivalents, more preferably 10–1000 molar equivalents. That is, the chromogen is used usually at a concentration of 0.01–100 mM, preferably 0.1–10 mM.

Ascorbate oxidase (ASOD) and peroxidase are used at a concentration of 0.1–100 U/ml, preferably 0.2–50 U/ml.

The reducing agent is used in an equimolar amount with oxidized ascorbic acid or more, preferably 1–1000 molar equivalents, more preferably 10–100 molar equivalents. That is, the reducing agent is used usually at a concentration of 0.01–100 mM, preferably 1–10 mM.

The buffer agent is used at a concentration of 1–2000 mM, preferably 5–1000 mM. The pH of the buffer solution is determined according to the stability of the enzymes and the reagents and the reaction conditions, which is usually in the range of 2–10, preferably 3–9.

The compound which is capable of deactivating the reducing agent is used at 1–10 fold concentration, preferably 2–5 fold concentration based on the reducing agent used to reduce oxidized ascorbic acid.

The content or concentration of each component of the reagent for the determination and the reagents constituting the kit may vary according to their composition and usage. The concentration of each component may be adjusted when the component is added to an aqueous medium to prepare a reaction solution or when the reagent itself is prepared as a reaction solution.

The amount of oxidized ascorbic acid in a sample can be obtained by subtracting the amount of reduced ascorbic acid from the total amount of reduced ascorbic acid and oxidized ascorbic acid.

In the present invention, any chromogen which is hardly affected by reducing substances in a reaction for the determination of hydrogen peroxide can be used. Preferred examples are compounds represented by general formulae (I) and (II) shown below.

General formula (I)

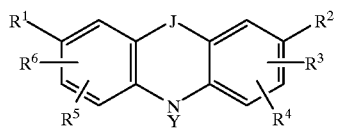

(I)

General formula (II)

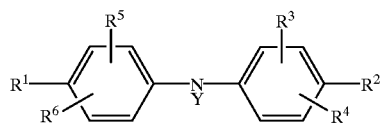

(II)

{In the above general formulae (I) and (II), Y represents a hydrogen atom or a group represented by general formula (III):

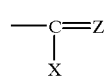

(III)

(wherein Z represents oxygen or sulfur; and X represents hydrogen, alkyl, alkenyl, aryl, mono-substituted amino or unsubstituted amino); $R^1$ represents hydroxy, mono- or di-substituted amino or unsubstituted amino; $R^2$ represents hydrogen, hydroxy, alkyl, alkoxy, aryl, alkenyl, mono- or di-substituted amino or unsubstituted amino; $R^3$, $R^4$, $R^5$ and $R^6$, which may be the same or different, each represents hydrogen, alkyl, alkenyl, alkanoyl, aroyl, aryl, halogen, nitro, sulfo, carboxy, hydroxy, alkoxy or a group represented by general formula (IV), (V), (VI), (VII) or (VIII):

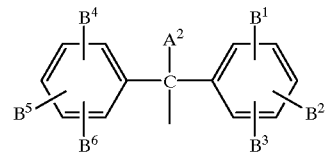

(IV)

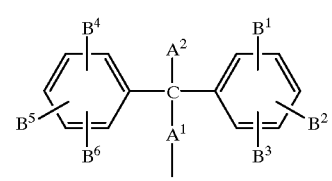

(V)

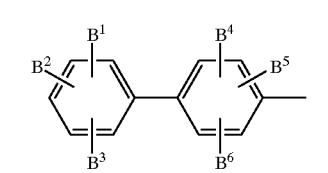

(VI)

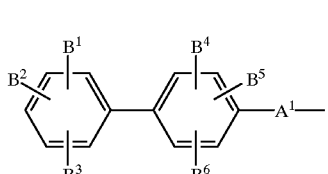

(VII)

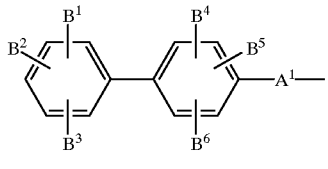

(VIII)

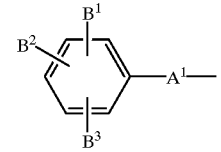

[wherein $A^1$ represents alkylene; $A^2$ represents hydrogen, hydroxy, alkyl, alkoxy, aryl, alkenyl, alicyclic alkyl, mono- or di-substituted amino or unsubstituted amino; and $B^1$, $B^2$, $B^3$, $B^4$, $B^5$ and $B^6$, which may be the same or different, each represents hydrogen, alkyl, alkenyl, alkanoyl, aroyl, aryl, halogen, nitro, sulfo, carboxy, hydroxy, alkoxy or hydroxy-substituted alkyl]; or $R^3$ and $R^4$, or $R^5$ and $R^6$ are combined together to form alkenylene; and J represents oxygen, sulfur or a group represented by general formula (IX) or (XI):

(IX)

(XI)

[wherein $R^7$ and $R^8$, which may be the same or different, each represents hydrogen, alkyl or alkenyl]}.

In the definitions of the above groups, the alkyl and the alkyl moiety of the alkoxy and the hydroxy-substituted alkyl include straight-chain or branched alkyl groups having 1–6 carbon atoms such as methyl, ethyl, propyl, isopropyl, butyl, isobutyl, sec-butyl, tert-butyl, pentyl, 2-pentyl, 3-pentyl, isoamyl and hexyl. The hydroxy-substituted alkyl has 1–2 hydroxy substituents.

The alkanoyl includes alkanoyl groups having 1–6 carbon atoms such as formyl, acetyl, propionyl, butyryl, isobutyryl, valeryl, isovaleryl and pivaloyl.

The alicyclic alkyl includes alicyclic alkyl groups having 3–8 carbon atoms such as cyclopropyl, cyclobutyl, cyclopentyl, cyclohexyl, cycloheptyl and cyclooctyl. The alkenyl includes straight-chain or branched alkenyl groups having 2–6 carbon atoms such as vinyl, propenyl, butenyl, pentenyl and hexenyl. Examples of the aryl and the aryl moiety of the aroyl are phenyl and naphthyl.

The halogen includes fluorine, chlorine, bromine and iodine atoms.

The alkylene includes alkylene groups having 1–6 carbon atoms such as methylene, ethylene, methylmethylene, propylene, methylethylene, ethylmethylene, butylene, 1-methylpropylene, 2-methylpropylene, ethylethylene, propylmethylene, pentylene, methylbutylene, ethylbutylene, butylmethylene and hexylene.

The alkenylene includes alkenylene groups having 3–4 carbon atoms such as —CH=CH—CH$_2$— and —CH=CH—CH=CH—.

Examples of the substituents in the mono- or di-substituted amino in the definitions of $R^1$, $R^2$ and $A^2$ are substituted or unsubstituted alkyl, aryl, alicyclic alkyl, alkanoyl, aroyl, alkenyl, alkoxycarbonyl, alkoxy, alkoxysulfonyl and carbamoyl.

The alkyl, the alkanoyl, the alkoxy, the aryl, the aroyl, the alicyclic alkyl and the alkenyl have the same significances as defined above. The alkyl moiety of the alkoxycarbonyl and the alkoxysulfonyl has the same significance as the above alkyl.

The substituted alkyl has 1–3 substituents which are the same or different. Examples of the substituents are hydroxy, sulfo, aryl, alkanoyl and aroyl.

The aryl, the alkanoyl and the aroyl have the same significances as defined above.

Examples of the substituents in the mono-substituted amino in the definition of X are alicyclic alkyl, substituted or unsubstituted alkyl, and substituted or unsubstituted aryl. The alicyclic alkyl, the alkyl and the aryl have the same significances as defined above.

The substituted alkyl has 1–2 substituents which are the same or different. Examples of the substituents are alkoxycarbonyl, alkoxycarbonylamino, alkoxycarbonylaminophenyl and alkoxycarbonylaminoalkylphenyl. The alkyl moiety of the alkoxy in said substituents has the same significance as defined above, and the alkyl moiety of the alkoxycarbonylaminoalkylphenyl has the same significance as the above alkylene.

The substituted aryl has 1–2 substituents which are the same or different. Examples of the substituents are halogen, amino, sulfo, alkyl, alkoxy, alkanoyl, alkoxycarbonyl, alkoxycarbonylamino and alkoxycarbonylaminoalkyl. The alkyl, the alkoxy, the alkanoyl, the alkoxycarbonyl, the alkoxycarbonylamino, the alkoxycarbonylaminoalkyl and the halogen have the same significances as defined above.

Specific examples of the compounds represented by general formulae (I) and (II) include the compounds described in JP-A-29297/82 (U.S. Pat. No. 4,384,042), JP-A-218069/85 and JP-A-128799/89, JP-A-145352/81 (U.S. Pat. No. 4,851,353) and JP-A-182361/84 (U.S. Pat. No. 4,916,058).

Particularly preferred examples of the compounds represented by general formula (I) are 10-N-carboxymethylcarbamoyl-3,7-bis(dimethylamino)-10H-phenothiazine (hereinafter abbreviated as CCAP) and 10-N-methylcarbamoyl-3,7-bis(dimethylamino)-10H-phenothiazine (hereinafter abbreviated as MCDP). Particularly preferred examples of the compounds represented by general formula (II) are sodium salt of N-(carboxymethylaminocarbonyl)-4,4'-bis(dimethylamino) diphenylamine (hereinafter abbreviated as DA-64), 4,4'-bis (dimethylamino)diphenylamine and bis[3-bis(4-chlorophenyl)methyl-4-dimethylaminophenyl]amine (hereinafter abbreviated as BCMA). These chromogens can be synthesized according to, for example, the method described in JP-A-29297/82 (U.S. Pat. No. 4,384,042).

As the ASOD, ascorbate oxidase derived from microorganisms belonging to the genus Eupenicillium (JP-A-23971/96), Trichoderma or Mortierella (JP-A-209770/94), or Pleurotus [J. Biol. Chem., 271, 3105 (1996)], plants, or microorganisms obtained by recombinant DNA techniques can be employed. Commercially available ones (for example, a product of Amano Pharmaceutical Co., Ltd.) can also be used.

As the peroxidase, commercially available ones can be employed as well as ones extracted from microorganisms, animals and plants.

The reducing agent capable of converting oxidized ascorbic acid into reduced ascorbic acid includes SH group-containing compounds, phosphines, diphosphanes, sulfites, dithionites, ferrous salts and borohydrides.

The SH group-containing compounds include amino acids or peptides such as N-acetylcysteine, reduced cysteine and reduced glutathione, alcohols such as dithiothreitol (DTT), dithioerythritol, mercaptoethanol and thioglycerol, carboxylic acids such as thioglycolic acid, saccharides such as thioglucose, and thiouronium salts such as 2-aminoethylisothiouronium bromide.

The phosphines include substituted or unsubstituted phosphines. The unsubstituted phosphine means $PH_3$ (phosphine).

The substituted phosphine has 1–3 substituents which are the same or different. Examples of the substituents are substituted or unsubstituted alkyl, substituted or unsubstituted aryl, a substituted or unsubstituted aromatic heterocyclic group, substituted or unsubstituted amino, substituted or unsubstituted carbamoyl, substituted or unsubstituted alkoxy, substituted or unsubstituted alkanoyl, substituted or unsubstituted aroyl, and substituted or unsubstituted sulfo.

The phosphines having one substituent, those having 2 substituents and those having 3 substituents are called primary phosphines, secondary phosphines and tertiary phosphines, respectively.

The diphosphanes include substituted or unsubstituted diphosphanes. The unsubstituted diphosphane means $P_2H_4$ (diphosphane).

The substituted diphosphane has 1–4 substituents which are the same or different. Examples of the substituents are substituted or unsubstituted alkyl, substituted or unsubstituted aryl, a substituted or unsubstituted aromatic heterocyclic group, substituted or unsubstituted amino, substituted or unsubstituted carbamoyl, substituted or unsubstituted alkoxy, substituted or unsubstituted alkanoyl, substituted or unsubstituted aroyl, and substituted or unsubstituted sulfo.

The substituted or unsubstituted alkyl and the alkyl moiety of the substituted or unsubstituted alkoxy and the substituted or unsubstituted alkanoyl, and the substituted or unsubstituted aryl and the aryl moiety of the substituted or unsubstituted aroyl mentioned above as the substituents in phosphines and diphosphanes have the same significances as the above alkyl and aryl.

Examples of the aromatic heterocyclic groups of the substituted or unsubstituted aromatic heterocyclic groups mentioned above as the substituents in phosphines and diphosphanes are pyridyl, pyrimidinyl, naphthyridinyl, furyl, thienyl, pyrazolinyl, imidazolyl, benzofuryl and dibenzofuryl.

The substituted alkyl has 1–3 substituents which are the same or different. Examples of the substituents are aryl, an aromatic heterocyclic group, alkoxy, alkanoyl, aroyl, amino, hydroxy, carboxy, sulfo, phospho, cyano and halogen. The aryl, the aromatic heterocyclic group, the alkoxy, the alkanoyl, the aroyl and the halogen have the same significances as defined above.

The substituted aryl has 1–5 substituents which are the same or different. Examples of the substituents are alkyl, alkoxy, alkanoyl, aroyl, carboxy, alkoxycarbonyl, cyano, amino, sulfo, phospho and halogen. The alkyl, the alkoxy, the alkanoyl, the aroyl, the alkoxycarbonyl and the halogen have the same significances as defined above. The substituted aromatic heterocyclic group has 1–3 substituents which are the same or different, and said substituents include the same substituents as in the above substituted aryl.

The substituted amino and the substituted carbamoyl respectively have 1–2 substituents which are the same or different. The substituents include the same substituted or unsubstituted alkyl, substituted or unsubstituted aryl, substituted or unsubstituted aromatic heterocyclic group, alkanoyl, aroyl and alkoxycarbonyl as defined above.

The substituted alkoxy has 1–2 substituents which are the same or different. Examples of the substituents are amino, hydroxy, sulfo, phospho, cyano and the above halogen.

The substituents in the substituted sulfo include the same substituted or unsubstituted alkyl, substituted or unsubstituted aryl and substituted or unsubstituted aromatic heterocyclic group as defined above.

Examples of the primary phosphines are methylphosphine, ethylphosphine, propylphosphine, isobutylphosphine, phenylphosphine, 2-naphthylphosphine, 2-benzofuranylphosphine, 2-phosphinoethylamine, 4-(phosphinomethyl)imidazole, 1,2,4-butanetriyltris(phosphine), (phenylsulfonyl)phosphine and carbamoylphosphine.

Examples of the secondary phosphines are dimethylphosphine, diethylphosphine, diisopropylphosphine, diisoamylphosphine, diphenylphosphine, 3,3'-phosphinediyldipropionic acid, and 4,4'-phosphinediyldibenzoic acid.

Examples of the tertiary phosphines are trimethylphosphine, triethylphosphine, tri-n-butylphosphine, tri-n-hexylphosphine, triphenylphosphine, methyldiphenylphosphine, dimethylphenylphosphine, phosphinetriyltridimethylamine, phosphinetriyltridiethylamine, tris(2 -methylphenyl)phosphine, tris(3-methylphenyl)phosphine, tris(4-methylphenyl)phosphine, tris(4-methoxyphenyl)phosphine, phosphinetriyltriacetic acid, 3,3',3"-phosphinetriyltripropionic acid, 4,4',4"-phosphinetriyltribenzoic acid, tris(hydroxymethyl)phosphine, 2,2',2"-phosphinetriyltriethylcyanide, ethyl(phenyl)propylphosphine and acetyldiethylphosphine.

The sulfites and dithionites include those of alkali metals such as lithium, potassium and sodium, and those of alkaline earth metals such as magnesium and calcium.

The ferrous salts include ferrous halide, ferrous sulfate and ferrous nitrate. The halogen has the same significance as defined above.

Preferred reducing agents are SH group-containing compounds.

The compound capable of deactivating the reducing agent includes SH reagents and oxides, which are selected according to the kind of the reducing agent to be used. In cases where an SH group-containing compound is used as the reducing agent, SH reagents such as an oxidizing agent, a mercapto-forming agent and an alkylating agent are preferably used. An alkylating agent is particularly preferred.

Examples of the oxidizing agents are 5,5'-dithiobis(2-nitrobenzoic acid), 2,2'-dipyridyldisulfide, tetrathionic acid, 2,6-dichlorophenolindophenol and oxidized glutathione. Examples of the mercapto-forming agents are p-mercuribenzoic acid and p-mercuribenezenesulfonic acid, and examples of the alkylating agents are iodoacetic acid, iodoacetamide and N-ethylmaleimide. Examples of the oxides are iodates such as potassium iodate.

Examples of the buffer agents are lactate, citrate, acetate, succinate, glycine salt, 3,3-dimethylglutarate, phthalate, phosphate, triethanolamine salt, diethanolamine salt, borate, barbiturate, tris(hydroxymethyl)aminomethane salt, imidazole-acetate, malate, oxalate, carbonate and Good's buffer agent.

An example of the enzyme-activating agent is dehydroacetic acid. Examples of the preservatives are sodium azide and streptomycin sulfate. Examples of the stabilizers are metal chelating agents such as ethylenediaminetetraacetic acid (hereinafter abbreviated as EDTA), and examples of the other stabilizers for enzymes are polysaccharides such as soluble starch and derivatives thereof, proteins such as albumin and globulin, and water-soluble high-molecular weight compounds such as polyethylene glycol. An example of the surfactant is Triton X-100.

As the aqueous medium, water-containing liquids such as a buffer solution, physiological saline and distilled water can be used, and preferred is a buffer solution.

The compounds and enzymes described above are listed in the reagent catalogues published by Tokyo Kasei Kogyo Co., Ltd., Dojin Kagaku Institute, Daito Kagaku Co., Ltd., Wako Pure Chemical Industries, Ltd., Seishin Co., Ltd., Nacalai Tesque, Inc., Aldrich, Pierce, etc., and are commercially available.

Test Examples are shown below.

TEST EXAMPLE 1

Effect of Reduced Ascorbic Acid on the Color Development of a Reaction Solution

In the test, sodium N-(2-hydroxy-3-sulfopropyl)-3,5-dimethoxyaniline (hereinafter abbreviated as HSDA) and 4-aminoantipyrine (hereinafter abbreviated as 4-AA), and N-ethyl-N-(3-methylphenyl)-N'-succinylethylenediamine (hereinafter abbreviated as EMSE) and 4-AA were used as Trinder's reagents, and CCAP and BCMA were used as leuco-chromogens.

Piperazine-N,N'-bis(2-ethanesulfonic acid) (hereinafter abbreviated as PIPES) buffer solution (10.0 mM, pH 6.0) containing reduced ascorbic acid at a concentration shown in Table 1, 6.25 U/ml peroxidase and one of the above chromogens (0.086 mM) was heated at 37° C. for 5 minutes. To the resulting solution was added hydrogen peroxide to a concentration of 25 $\mu$M to start reaction. After the reaction reached equilibrium, the absorbance of the reaction solution was measured at the maximum absorption wavelength of the used chromogen. The change in absorbance resulting from the reaction is shown in Table 1.

TABLE 1

| Chromogen | Reduced ascorbic acid (μM) | | | | |
|---|---|---|---|---|---|
| | 0 | 10 | 19 | 38 | 95 |
| HSDA 4-AA | 0.152 | 0.141 | 0.130 | 0.117 | 0.089 |
| EMSE 4-AA | 0.286 | 0.266 | 0.240 | 0.212 | 0.160 |
| CCAP | 0.804 | 0.755 | 0.691 | 0.624 | 0.473 |
| BCMA | 0.329 | 0.309 | 0.281 | 0.256 | 0.193 |

As shown in Table 1, coloration reaction using any of EMSE and 4-AA, and HSDA and 4-AA, which are Trinder's reagents, and CCAP and BCMA, which are leuco-chromogens, is inhibited by the presence of reduced ascorbic acid.

TEST EXAMPLE 2

Effect of Dithiothreitol on the Color Development of a Reaction Solution

The same procedure as in Test Example 1 was repeated, except that dithiothreitol was used in place of reduced ascorbic acid.

The change in absorbance resulting from the reaction is shown in Table 2.

TABLE 2

| Chromogen | Dithiothreitol concentration (mM) | | | | |
|---|---|---|---|---|---|
| | 0 | 1.1 | 2.2 | 4.4 | 8.8 |
| HSDA 4-AA | 0.152 | 0 | 0 | 0 | 0 |
| EMSE 4-AA | 0.286 | 0 | 0 | 0 | 0 |
| CCAP | 0.804 | 0.800 | 0.802 | 0.613 | 0.455 |
| BCMA | 0.329 | 0.343 | 0.326 | 0.251 | 0.186 |

As shown in Table 2, coloration reaction using any of EMSE and 4-AA, and HSDA and 4-AA, which are Trinder's reagents, and CCAP and BCMA, which are leuco-chromogens, is inhibited by the presence of dithiothreitol.

TEST EXAMPLE 3

A 10.0 mM PIPES buffer solution (pH 6.0) containing 6.25 U/ml peroxidase and one of the chromogens shown in Table 3 (0.086 mM) was preliminarily heated at 37° C. for 5 minutes, and hydrogen peroxide was added thereto to a concentration of 15 μM to start reaction (Reaction system 1).

Separately, a 10.0 mM PIPES buffer solution (pH 6.0) containing 2.76 U/ml ASOD (ascorbate oxidase, Amano Pharmaceutical Co., Ltd., Type III), 6.25 U/ml peroxidase and one of the chromogens (0.086 mM) was heated at 37° C. for 5 minutes, and reduced ascorbic acid was added thereto to a concentration of 15 μm to start reaction (Reaction system 2).

In each reaction system, the absorbance of the reaction solution was measured at the maximum absorption wavelength of the used chromogen, at the start of the reaction and after the reaction reached equilibrium. The change in absorbance resulting from the reaction of each reaction system is shown in Table 3.

TABLE 3

| Chromogen | Reaction system | Absorbance |
|---|---|---|
| HSDA 4-AA | Reaction system 1 | 0.091 |
| HSDA 4-AA | Reaction system 2 | 0.0 |
| EMSE 4-AA | Reaction system 1 | 0.171 |
| EMSE 4-AA | Reaction system 2 | 0.0 |
| CCAP | Reaction system 1 | 0.487 |
| CCAP | Reaction system 2 | 0.488 |
| BCMA | Reaction system 1 | 0.319 |
| BCMA | Reaction system 2 | 0.315 |

As shown in Table 3, when EMSE and 4-AA, or HSDA and 4-AA was used as the chromogen, coloration of the reaction solution by the reaction of hydrogen peroxide formed by the enzyme reaction using ASOD with said chromogen was hardly detected. On the other hand, when leuco-chromogen CCAP or BCMA was used, the formation of a pigment by the reaction of hydrogen peroxide formed by the enzyme reaction with said chromogen was satisfactorily recognized, which shows that the present reaction system enables the determination of reduced ascorbic acid.

TEST EXAMPLE 4

A 10.0 mM PIPES buffer solution (pH 6.0) containing 2.76 U/ml ASOD (ascorbate oxidase, Amano Pharmaceutical Co., Ltd., Type III), 6.25 U/ml peroxidase and 0.086 mM CCAP was heated at 37° C. for 5 minutes, and reduced ascorbic acid was added thereto to a concentration of 7.5 μM to start reaction (non-DTT-added system).

Separately, a 10.0 mM PIPES buffer solution (pH 6.0) containing 2.75 U/ml ASOD, 6.25 U/ml peroxidase, 0.086 mM CCAP and 2.16 mg/dl dithiothreitol was heated at 37° C. for 5 minutes, and ascorbic acid was added thereto to a concentration of 7.5 μM to start reaction (DTT-added system).

In each reaction system, the absorbance of the reaction solution was measured at 660 nm at the start of the reaction and after the reaction reached equilibrium. The change in absorbance resulting from the reaction of each reaction system is shown in Table 4.

TABLE 4

| Ascorbic acid | Absorbance | |
|---|---|---|
| concentration (μM) | Non-DTT-added | DTT-added |
| 7.5 | 0.240 | 1.686 |

DTT addition: 2.2 mM

As shown in Table 4, the degree of color development of the present reaction is greatly enhanced by the addition of dithiothreitol, which suggests that the present method enables the determination of reduced ascorbic acid with high sensitivity.

BEST MODES FOR CARRYING OUT THE INVENTION

Certain embodiments of the present invention are illustrated in the following Examples.

The following reagent solutions were prepared for use in Examples.

* Reagent solutions for the determination of reduced ascorbic acid

Reagent solution A-1

| | |
|---|---|
| CCAP | 0.089 mM |
| Potassium phosphate buffer (pH 6.0) | 97.4 mM |
| Peroxidase | 6.5 U/ml |
| ASOD | 3.1 U/ml |

Reagent solution A-2

| | |
|---|---|
| BCMA | 0.125 mM |
| Potassium phosphate buffer (pH 6.0) | 97.4 mM |
| Peroxidase | 6.5 U/ml |
| ASOD | 3.1 U/ml |

Reagent solution A-3

| | |
|---|---|
| MCDP | 0.115 mM |
| Potassium phosphate buffer (pH 6.0) | 97.4 mM |
| Peroxidase | 6.5 U/ml |
| ASOD | 3.1 U/ml |

* Reagent solutions for the determination of total ascorbic acid

Reagent solution B-1

| | |
|---|---|
| CCAP | 0.089 mM |
| Potassium phosphate buffer (pH 6.0) | 97.4 mM |
| Peroxidase | 6.5 U/ml |
| ASOD | 3.1 U/ml |
| Dithiothreitol | 2.16 mM |

Reagent solution B-2

| | |
|---|---|
| BCMA | 0.125 mM |
| Potassium phosphate buffer (pH 6.0) | 97.4 mM |
| Peroxidase | 6.50 /ml |
| ASOD | 3.1 U/ml |
| Dithiothreitol | 2.16 mM |

* Kit of reagent solutions for the determination of reduced ascorbic acid

Kit A-4
Reagent solution A-4a

| | |
|---|---|
| Potassium phosphate buffer (pH 6.0) | 9.5 mM |
| CCAP | 0.115 mM |

Reagent solution A-4b

| | |
|---|---|
| Potassium phosphate buffer (pH 6.0) | 86.7 mM |
| Peroxidase | 25.0 U/ml |
| ASOD | 12.0 U/ml |

* Kit of reagent solutions for the determination of total ascorbic acid

Kit C-1
Reagent solution C-1a

| | |
|---|---|
| Potassium phosphate buffer (pH 6.0) | 9.5 mM |
| Dithiothreitol | 0.58 mM |
| CCAP | 0.115 mM |

Reagent solution C-1b

| | |
|---|---|
| Potassium phosphate buffer (pH 6.0) | 86.7 mM |
| N-ethylmaleimide | 4.27 mM |
| Peroxidase | 25.0 U/ml |
| ASOD | 12.0 U/ml |

EXAMPLE 1

As the standard solutions, 10 mM glycine-hydrochloric acid buffer solutions (pH 3.0) containing varied concentrations of reduced ascorbic acid were prepared.

After 2.9 ml of Reagent solution A-1 was heated at 37° C. for 5 minutes, 0.1 ml of each ascorbic acid standard solution was added thereto, followed by reaction at 37° C. for 5 minutes. After the reaction was completed, the increase in absorbance of the reaction solution was measured at 660 nm.

Figure 1:
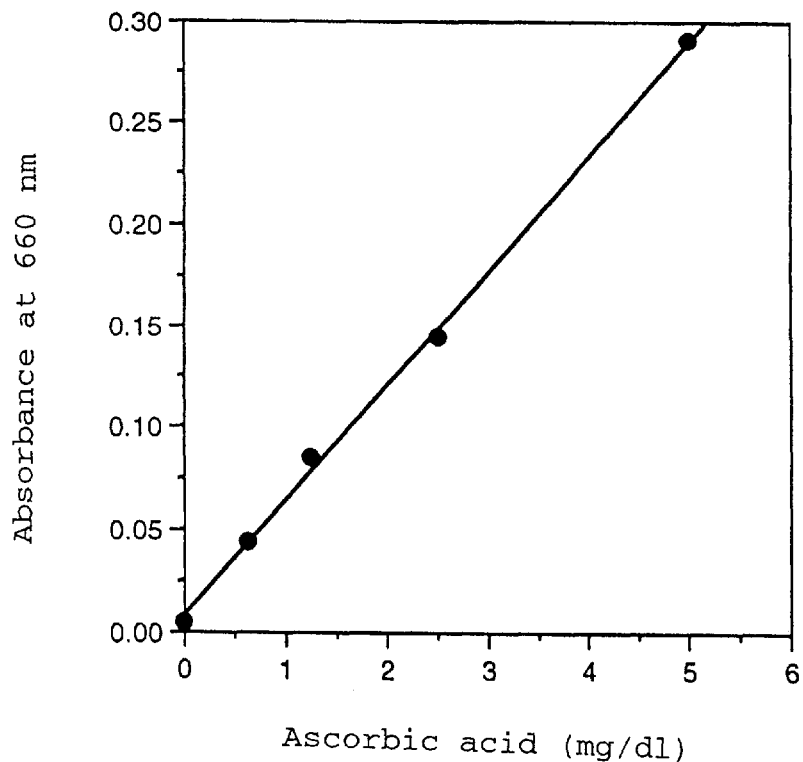
FIG. 1 is a calibration curve which shows the correlation between the concentration of reduced ascorbic acid and the absorbance in the determination using Reagent solution A-1.

The correlation between the concentration of reduced ascorbic acid and the absorbance is shown in FIG. 1. The concentration of reduced ascorbic acid solution added (mg/dl) is plotted as abscissa and the absorbance at 660 nm as ordinate. It is clear from the drawing that the amount of reduced ascorbic acid in a test sample can be successfully measured utilizing the proportional relation of the content of reduced ascorbic acid in the test sample to the absorbance. Reduced ascorbic acid can be precisely determined to the extent of about 0.2 mg/dl.

EXAMPLE 2

Figure 2:
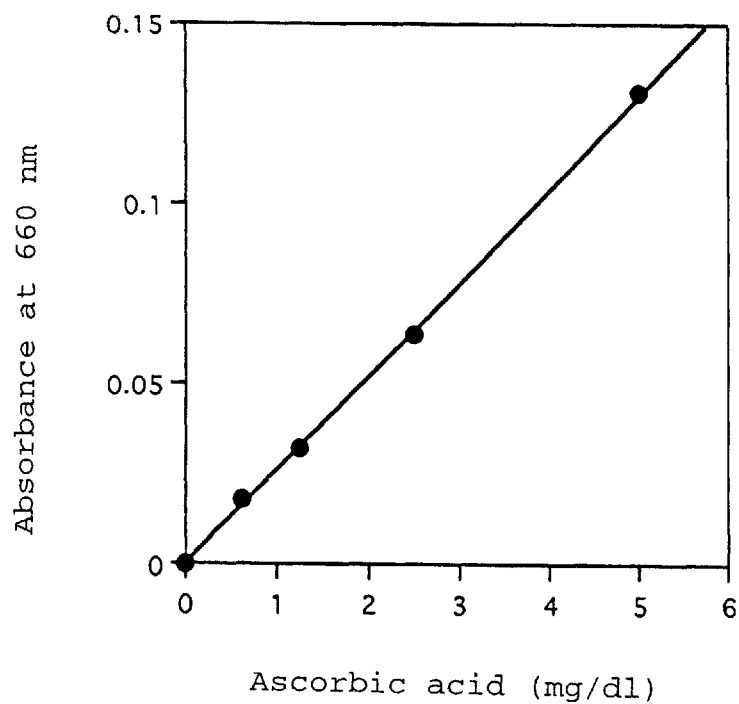
FIG. 2 is a calibration curve which shows the correlation between the concentration of reduced ascorbic acid and the absorbance in the determination using Reagent solution A-2.

The same procedure as in Example 1 was repeated, except that Reagent solution A-2 was used in place of Reagent solution A-1, and the increase in absorbance of the reaction solution was measured at 755 nm. The results are shown in FIG. 2.

It is clear from the drawing that the amount of reduced ascorbic acid in a test sample can be successfully measured utilizing the proportional relation of the content of reduced ascorbic acid in the test sample to the absorbance. Reduced ascorbic acid can be precisely determined to the extent of about 0.2 mg/dl.

EXAMPLE 3

The concentration of reduced ascorbic acid in fresh serum samples 1–3 was determined using Reagent solutions A-1, A-2 and A-3 according to the method of Example 1. The absorbance of the reaction solution was measured at the maximum absorption wavelength of the chromogen used.

For comparison, the concentration of reduced ascorbic acid in said serum samples was determined using a kit for the determination of ascorbic acid (Boehringer Mannheim, F-kit, L-ascorbic acid, Product No. 409677). The results are shown in Table 5.

TABLE 5

| | Ascorbic acid concentration (mg/dl) | | |
|---|---|---|---|
| Reagent used | Serum sample 1 | Serum sample 2 | Serum sample 3 |
| A-1 | 0.620 | 1.114 | 0.224 |
| A-2 | 0.622 | 1.115 | 0.236 |
| A-3 | 0.620 | 1.091 | 0.220 |
| F-kit | 0.630 | 1.150 | immeasurable |

As shown in Table 5, the values obtained by the method for the determination of the present invention were almost the same as those obtained by the method using F-kit. As for serum sample 3, the ascorbic acid concentration was not measurable by the use of F-kit because of low absorbance, but could be determined by the method of the present invention.

EXAMPLE 4

The total amount of reduced ascorbic acid and oxidized ascorbic acid was determined using Kit A-4 and Kit C-1.

Sample solutions were prepared by dissolving reduced ascorbic acid and oxidized ascorbic acid in 10 mM potassium phosphate buffer solutions (pH 6.0) so that the total amount thereof in each solution became 2.5 mg/dl as shown in Table 6.

To 2.2 ml each of Reagent solution A-4a and Reagent solution C-1a was added 50 μl of each sample solution, followed by heating at 37° C. for 5 minutes. To the resulting mixtures were respectively added 0.75 ml each of Reagent solution A-4b and Reagent solution C-1b, followed by reaction at 37° C. for 5 minutes. After the reaction was completed, the increase in absorbance of each reaction solution was measured at 660 nm. The results are shown in Table 6.

TABLE 6

| Ascorbic acid concentration (mg/dl) | | Absorbance | |
|---|---|---|---|
| Reduced form | Oxidized form | Kit A-4 | Kit C-1 |
| 0.0 | 2.500 | 0.006 | 0.285 |
| 0.625 | 1.875 | 0.032 | 0.284 |
| 1.25 | 1.25 | 0.058 | 0.290 |
| 1.875 | 0.625 | 0.094 | 0.286 |
| 2.500 | 0.0 | 0.220 | 0.283 |

As shown in Table 6, the absorbance proportional to the amount of reduced ascorbic acid was obtained by the method using Kit A-4, and the absorbance corresponding to the total amount of reduced ascorbic acid and oxidized ascorbic acid was obtained by the method using Kit C-1.

EXAMPLE 5

Ascorbic acid determination was carried out using Kit C-1 according to the method of Example 4 on 50 μl each of serum sample 1 used in Example 3 and serum sample 1 which had been allowed to stand at room temperature for 6 hours. The determination on the same samples was also carried out in the same manner using F-kit. The results are shown in Table 7.

TABLE 7

| | Ascorbic acid concentration (mg/dl) | |
|---|---|---|
| Reagent used | Fresh blood | Stored blood |
| Kit C-1 | 0.652 | 0.602 |
| F-kit | 0.630 | immeasurable |

The result that the absorbance of the stored blood could not be measured by the use of F-kit, which is a kit for the determination of reduced ascorbic acid, shows that reduced ascorbic acid had been converted into oxidized ascorbic acid in the stored blood.

The value obtained on the sample wherein reduced ascorbic acid had been converted into oxidized ascorbic acid through standing for a long time was similar to that of the total amount of reduced ascorbic acid and oxidized ascorbic acid before standing. It is considered that the total amount of reduced ascorbic acid and oxidized ascorbic acid in the stored blood sample was smaller than that in the fresh blood sample because oxidized ascorbic acid had been irreversibly decomposed into 2,3-diketogulonic acid by storage. The reason why the value on the fresh blood obtained by the present method was higher than that in Example 3 is that oxidized ascorbic acid originally contained in the blood was measured together.

EXAMPLE 6

As the standard solutions, 10 mM glycine-hydrochloric acid buffer solutions (pH 3.0) containing varied concentrations of reduced ascorbic acid were prepared.

After 2.9 ml of Reagent solution B-1 was heated at 37° C. for 5 minutes, 0.1 ml of each reduced ascorbic acid standard solution was added thereto, followed by reaction at 37° C. for 20 minutes. After the reaction was completed, the increase in absorbance in reaction solution was measured at 660 nm.

Figure 3:
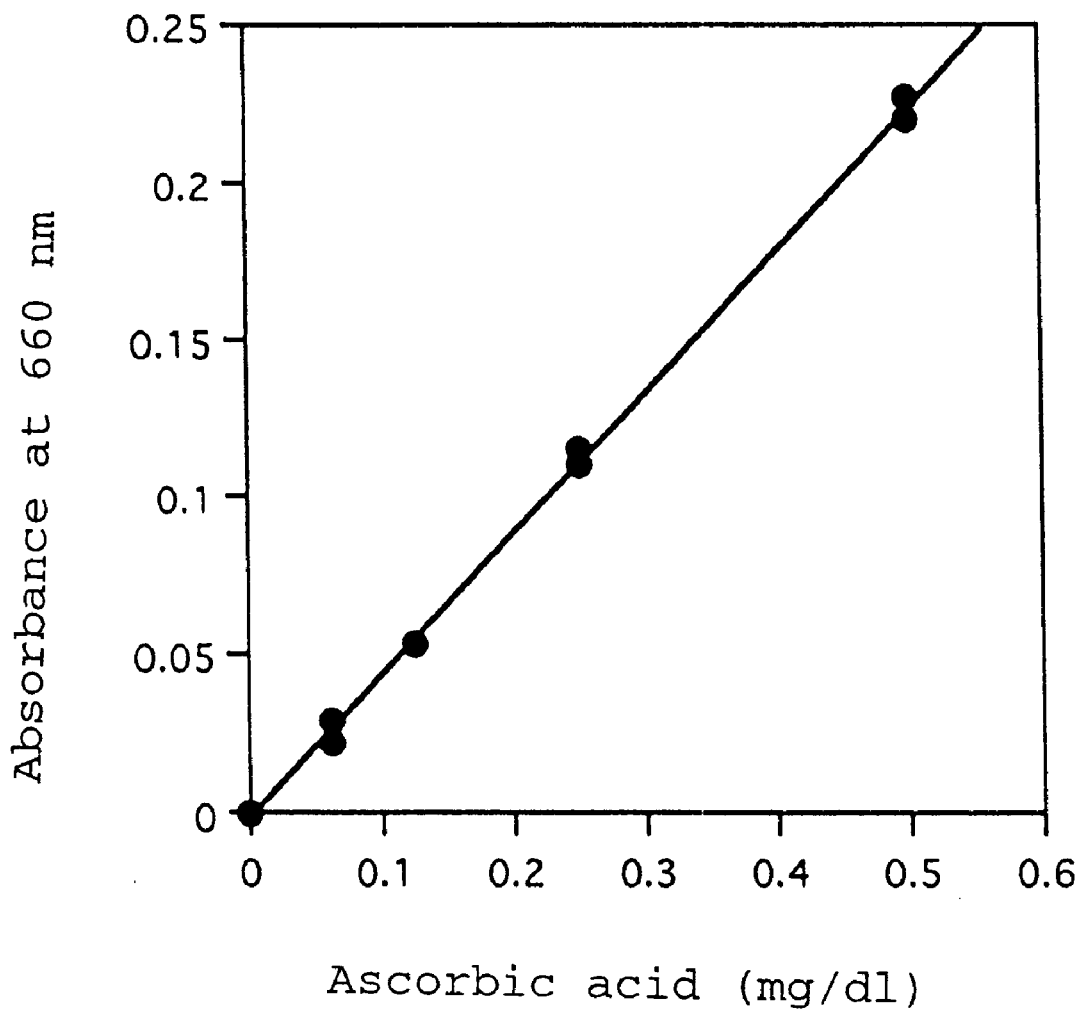
FIG. 3 is a calibration curve which shows the correlation between the concentration of reduced ascorbic acid and the absorbance in the determination using Reagent solution B-1.

The correlation between the concentration of reduced ascorbic acid and the absorbance is shown in FIG. 3. The concentration of reduced ascorbic acid added (mg/dl) is plotted as abscissa, and the absorbance at 660 nm as ordinate. It is clear from the drawing that a trace amount of reduced ascorbic acid in a test sample can be successfully determined utilizing the proportional relation of the content of reduced ascorbic acid in the test sample to the absorbance by the use of Reagent solution B-1 which is highly sensitive to reduced ascorbic acid. Reduced ascorbic acid can be precisely determined to the extent of about 0.05 mg/dl.

INDUSTRIAL APPLICABILITY

The present invention provides a method, a reagent and a kit for the determination of ascorbic acid which are useful in the field of diagnostic medicine.

What is claimed is:

1. A method for quantitative determination of ascorbic acid in a sample, comprising the steps of:

(a) selecting ascorbate oxidase which catalyzes the reaction of L-ascorbic acid with oxygen to form dehydroascorbic acid and hydrogen peroxide;

(b) selecting a chromogen represented by formulae (I) or (II):

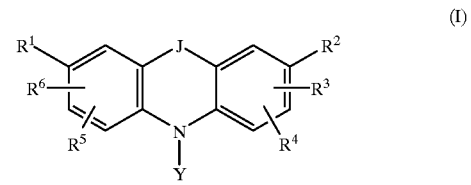

(I)

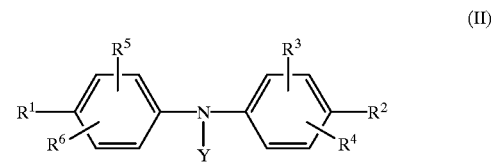

(II)

wherein

Y represents a hydrogen atom or a group represented by formula (III):

(III)

wherein Z represents oxygen or sulfur; and X represents hydrogen, alkyl, alkenyl, aryl, mono-substituted amino or unsubstituted amino;

$R^1$ represents hydroxy, mono- or di-substituted amino or unsubstituted amino;

$R^2$ represents hydrogen, hydroxy, alkyl, alkoxy, aryl, alkenyl, mono- or di-substituted amino or unsubstituted amino;

$R^3$, $R^4$, $R^5$ and $R^6$ independently represent hydrogen, alkyl, alkenyl, alkanoyl, aroyl, aryl, halogen, nitro, sulfo, carboxy, hydroxy, alkoxy or a group represented by formulae (IV), (V), (VI), (VII) or (VIII):

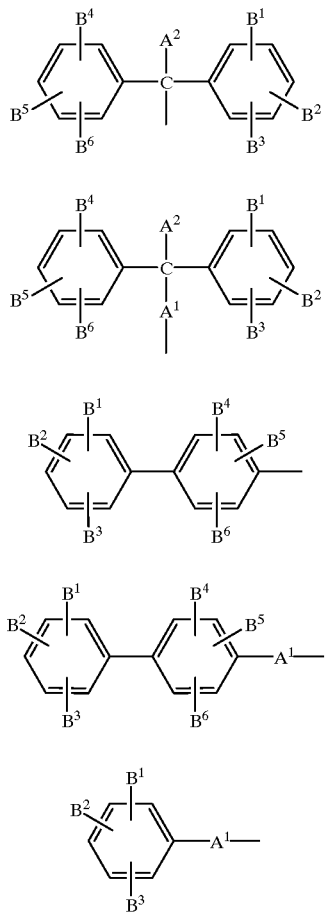

wherein $A^1$ represents alkylene; $A^2$ represents hydrogen, hydroxy, alkyl, alkoxy, aryl, alkenyl, alicyclic alkyl, mono- or di-substituted amino or unsubstituted amino; and $B^1$, $B^2$, $B^3$, $B^4$, $B^5$ and $B^6$ independently represent hydrogen, alkyl, alkenyl, alkanoyl, aroyl, aryl, halogen, nitro, sulfo, carboxy, hydroxy, alkoxy or hydroxy-substituted alkyl; or $R^3$ and $R^4$, or $R^5$ and $R^6$ are combined together to form alkenylene; and J represents oxygen, sulfur or a group represented by formula (IX) or (XI):

wherein $R^7$ and $R^8$ independently represent hydrogen, alkyl or alkenyl;

(c) reacting in an aqueous medium ascorbic acid in the sample with oxygen in the presence of the ascorbate oxidase, chromogen and peroxidase wherein pigment formation catalyzed by peroxidase from the chromogen and $H_2O_2$ which is produced from L-ascorbic acid in the sample by ascorbate oxidase is not substantially affected by presence of L-ascorbic acid;

(d) measuring an absorbance of the aqueous medium, wherein the absorbance is indicative of the quantity of ascorbic acid in the sample; and (e) comparing the absorbance with a calibration curve obtained using known amounts of ascorbic acid.

2. The method according to claim 1, wherein said aqueous medium comprises a reducing agent which converts dehydroascorbic acid into L-ascorbic acid.

3. The method according to claim 1, wherein said sample is admixed with a reducing agent which converts dehydroascorbic acid into L-ascorbic acid and then admixed with a compound which deactivates the reducing agent.

4. The method according to either of claims 1 or 2, wherein said chromogen is selected from the group consisting of 10-N-carboxymethylcarbamoyl-3,7-bis(dimethylamino)-10H-phenothiazine, 10-N-methylcarbamoyl-3,7-bis(dimethylamino)10H-phenothiazine, sodium salt of N-(carboxymethylaminocarbonyl)-4,4'-bis(dimethylamino)diphenylamine, 4,4'-bis(dimethylamino)diphenylamine, and bis[3-bis(4-chlorophenyl)methyl-4-dimethylaminophenyl]amine.

5. The method according to either of claims 2 or 3, wherein said reducing agent is selected from the group consisting of an SH group-containing compound, phosphine, diphosphane, sulfite, dithionite, ferrous salt and borohydride.

6. The method according to claim 5, wherein said reducing agent is dithiothreitol.

7. The method according to claim 3, wherein said compound which is which deactivates the reducing agent is an SH reagent.

8. The method according to claim 7, wherein said SH reagent is N-ethylmaleimide.

9. The method according to claim 7, wherein said reducing agent is dithiothreitol and said compound which is which deactivates the reducing agent is N-ethylmaleimide.

10. A composition for the determination of ascorbic acid comprising a chromogen, peroxidase, and ascorbate oxidase which catalyzes the reaction of L-ascorbic acid with oxygen to form dehydroascorbic acid and hydrogen peroxide, wherein said chromogen is a compound represented by formulae (I) or (II):

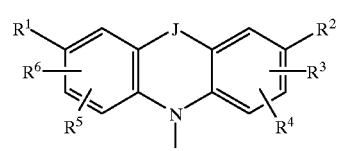

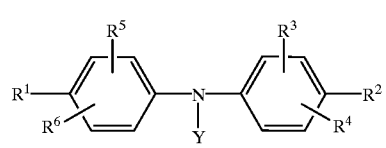

wherein

Y represents a hydrogen atom or a group represented by formula (III):

(III)

wherein Z represents oxygen or sulfur; and X represents hydrogen, alkyl, alkenyl, aryl, mono-substituted amino or unsubstituted amino;

$R^1$ represents hydroxy, mono- or di-substituted amino or unsubstituted amino;

$R^2$ represents hydrogen, hydroxy, alkyl, alkoxy, aryl, alkenyl, mono- or di-substituted amino or unsubstituted amino;

$R^3$, $R^4$, $R^5$ and $R^6$ independently represent hydrogen, alkyl, alkenyl, alkanoyl, aroyl, aryl, halogen, nitro, sulfo, carboxy, hydroxy, alkoxy or a group represented by general formulae (IV), (V), (VI), (VII) or (VIII):

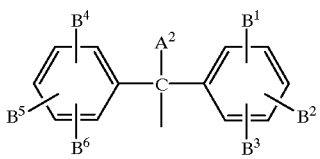
(IV)

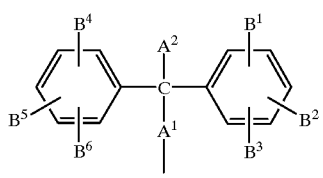
(V)

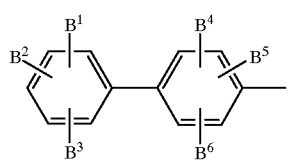
(VI)

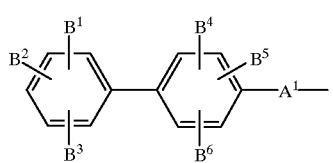
(VII)

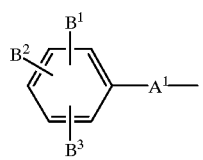
(VIII)

wherein $A^1$ represents alkylene; $A^2$ represents hydrogen, hydroxy, alkyl, alkoxy, aryl, alkenyl, alicyclic alkyl, mono- or di-substituted amino or unsubstituted amino; and $B^1$, $B^2$, $B^3$, $B^4$, $B^5$ and $B^6$ independently represent hydrogen, alkyl, alkenyl, alkanoyl, aroyl, aryl, halogen, nitro, sulfo, carboxy, hydroxy, alkoxy or hydroxy-substituted alkyl; or $R^3$ and $R^4$, or $R^5$ and $R^6$ are combined together to form alkenylene; and J represents oxygen, sulfur or a group represented by formula (IX) or (XI):

(IX)

(XI)

wherein $R^7$ and $R^8$ independently represent hydrogen, alkyl or alkenyl and wherein pigment formation catalyzed by peroxidase from the chromogen and $H_2O_2$ which is produced from L-ascorbic acid in the sample by ascorbate oxidase is not substantially affected by presence of L-ascorbic acid.

11. The composition according to claim 10, further comprising a reducing agent which converts dehydroascorbic acid into L-ascorbic acid.

12. The composition according to claim 11, further comprising a compound which deactivates said reducing agent.

13. The composition according to claim 10, wherein said chromogen is selected from the group consisting of 10-N-carboxymethylcarbamoyl-3,7-bis(dimethylamino)-10H-phenothiazine, 10-N-methylcarbamoyl-3,7-bis(dimethylamino)-10H-phenothiazine, sodium salt of N-(carboxymethylaminocarbonyl)-4,4'-bis(dimethylamino) diphenylamine, 4,4'-bis(dimethylamino)diphenylamine, and bis[3-bis(4-chlorophenyl)methyl-4-dimethylaminophenyl] amine.

14. The composition according to either of claims 11 or 12, wherein said reducing agent is dithiothreitol.

15. The composition according to claim 12, wherein said reducing agent is dithiothreitol and said compound which deactivates the reducing agent is N-ethylmaleimide.

16. A kit for the determination of reduced ascorbic acid consisting of a first reagent consisting essentially of ascorbate oxidase and peroxidase and a second reagent comprising a chromogen, wherein the chromogen is one of formulae (I) or (II):

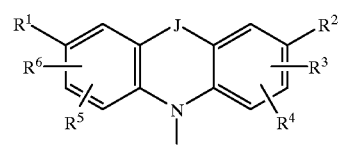
(I)

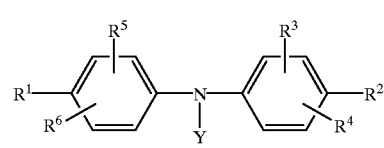
(II)

wherein

Y represents a hydrogen atom or a group represented by formula (III):

(III)

wherein Z represents oxygen or sulfur; and X represents hydrogen, alkyl, alkenyl, aryl, mono-substituted amino or unsubstituted amino;

$R^1$ represents hydroxy, mono- or di-substituted amino or unsubstituted amino;

$R^2$ represents hydrogen, hydroxy, alkyl, alkoxy, aryl, alkenyl, mono- or di-substituted amino or unsubstituted amino;

$R^3$, $R^4$, $R^5$ and $R^6$ independently represent hydrogen, alkyl, alkenyl, alkanoyl, aroyl, aryl, halogen, nitro, sulfo, carboxy, hydroxy, alkoxy or a group represented by general formulae (IV), (V), (VI), (VII) or (VIII):

(IV)

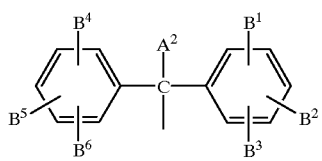

(V)

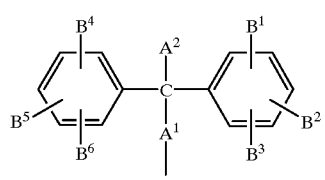

(VI)

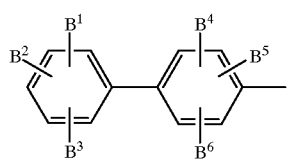

(VII)

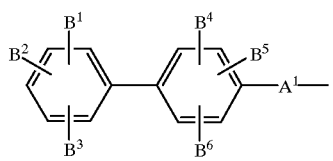

(VIII)

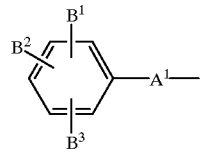

wherein $A^1$ represents alkylene; $A^2$ represents hydrogen, hydroxy, alkyl, alkoxy, aryl, alkenyl, alicyclic alkyl, mono- or di-substituted amino or unsubstituted amino; and $B^1$, $B^2$, $B^3$, $B^4$, $B^5$ and $B^6$ independently represent hydrogen, alkyl, alkenyl, alkanoyl, aroyl, aryl, halogen, nitro, sulfo, carboxy, hydroxy, alkoxy or hydroxy-substituted alkyl; or $R^3$ and $R^4$, or $R^5$ and $R^6$ are combined together to form alkenylene; and J represents oxygen, sulfur or a group represented by formula (IX) or (XI):

(IX)

(XI)

wherein $R^7$ and $R^8$ independently represent hydrogen, alkyl or alkenyl.

17. A kit for the determination of ascorbic acid according to claim 16, wherein said second reagent further comprises a reducing reagent.

18. A kit for the determination of ascorbic acid according to claim 12, which further comprises a compound which deactivates the reducing agent.

19. The kit according to any one of claims 16–18, wherein said chromogen is selected from the group consisting of 10-N-carboxymethylcarbamoyl-3,7-bis(dimethylamino)-10H-phenothiazine, 10-N-methylcarbamoyl-3,7-bis(dimethylamino)-10H-phenothiazine, sodium salt of N-(carboxymethylaminocarbonyl)-4,4'-bis(dimethylamino) diphenylamine, 4,4'-bis(dimethylamino)diphenylamine, and bis[3-bis(4-chlorophenyl)methyl-4-dimethylaminophenyl] amine.

20. The kit according to either of claims 12 or 13, wherein said reducing agent is dithiothreitol.

21. The kit according to claim 18, wherein said reducing agent is dithiothreitol and said compound which deactivates the reducing agent is N-ethylmaleimide.

* * * * *

UNITED STATES PATENT AND TRADEMARK OFFICE
CERTIFICATE OF CORRECTION

PATENT NO. : 6,153,399  
DATED : November 28, 2000  
INVENTOR(S) : Kinya Fujishiro et al.

Page 1 of 1

It is certified that error appears in the above-identified patent and that said Letters Patent is hereby corrected as shown below:

In the Drawings,
In sheet 1 of 2, Figure 2, "Absorbance at 660 nm" should read -- Absorbance at 755 nm --.

Column 1,
Line 56, "can not" should read -- cannot --.

Column 18,
Lines 35 and 40, "which is" should be deleted.

Column 22,
Line 36, "claim 12," should read -- claim 17, --; and
Line 46, "claims 12 or 13," should read -- claims 17 or 18, --.

Signed and Sealed this

First Day of January, 2002

Attest:

Attesting Officer

JAMES E. ROGAN
Director of the United States Patent and Trademark Office